US011690849B2

United States Patent
Wang et al.

(10) Patent No.: US 11,690,849 B2
(45) Date of Patent: *Jul. 4, 2023

(54) METHOD OF TREATING DEMENTIA

(71) Applicant: LA PharmaTech Inc., Blacksburg, VA (US)

(72) Inventors: Jianmin Wang, Blacksburg, VA (US); Geping Cui, Beijing (CN)

(73) Assignee: LA PharmaTech Inc., Blacksburg, VA (US)

( * ) Notice: Subject to any disclaimer, the term of this patent is extended or adjusted under 35 U.S.C. 154(b) by 82 days.

This patent is subject to a terminal disclaimer.

(21) Appl. No.: 17/459,868

(22) Filed: Aug. 27, 2021

(65) Prior Publication Data

US 2022/0000882 A1  Jan. 6, 2022

Related U.S. Application Data

(63) Continuation of application No. 16/831,330, filed on Mar. 26, 2020, now Pat. No. 11,116,773, which is a continuation of application No. 16/426,121, filed on May 30, 2019, now Pat. No. 10,639,316, and a continuation-in-part of application No. 16/424,788, filed on May 29, 2019, now Pat. No. 10,946,026, and a continuation-in-part of application No. 16/418,614, filed on May 21, 2019, now Pat. No. 10,639,315, and a continuation-in-part of application No. PCT/US2019/033359, filed on May 21, 2019, said application No. 16/426,121 is a continuation of application No. 16/398,845, filed on Apr. 30, 2019, now Pat. No. 10,639,314, said application No. 16/831,330 is a continuation-in-part of application No. PCT/US2019/029885, filed on Apr. 30, 2019, and a continuation-in-part of application No. PCT/US2019/027293, filed on Apr. 12, 2019, said application No. 16/424,788 is a continuation of application No. 16/382,885, filed on Apr. 12, 2019, now Pat. No. 10,966,989.

(51) Int. Cl.
*A61K 31/55* (2006.01)
*A61P 25/28* (2006.01)
*A61K 9/00* (2006.01)

(52) U.S. Cl.
CPC ............ *A61K 31/55* (2013.01); *A61K 9/0053* (2013.01); *A61P 25/28* (2018.01)

(58) Field of Classification Search
CPC ................. A61K 31/55; A61P 25/28
See application file for complete search history.

(56) References Cited

U.S. PATENT DOCUMENTS

| | | |
|---|---|---|
| 4,871,733 A | 10/1989 | Sunshine et al. |
| 5,068,233 A | 11/1991 | Achterrath-Tuckerman et al. |
| 5,086,050 A | 2/1992 | Hettche et al. |
| 5,110,814 A | 5/1992 | Engel et al. |
| 5,430,029 A | 7/1995 | Biella et al. |
| 5,958,964 A | 9/1999 | Pappolla |
| 5,994,357 A | 11/1999 | Theoharides |
| 6,008,221 A | 12/1999 | Smith et al. |
| 6,017,909 A | 1/2000 | Hettche et al. |
| 6,191,133 B1 | 2/2001 | Coppen |
| 6,200,607 B1 | 3/2001 | Bridgeman |
| 6,849,621 B2 | 2/2005 | Rosenblum et al. |
| 7,022,687 B1 | 4/2006 | Szelenyi et al. |
| 7,220,735 B2 | 5/2007 | Ting et al. |
| 7,355,042 B2 | 4/2008 | Edgar et al. |
| 7,384,981 B2 | 6/2008 | Kiliaan et al. |
| 7,615,550 B2 | 11/2009 | Heightman et al. |
| 7,786,161 B2 | 8/2010 | Tani et al. |
| 7,888,391 B2 | 2/2011 | Kiliaan et al. |
| 8,071,073 B2 | 12/2011 | Dang et al. |
| 8,168,620 B2 | 5/2012 | Lulla et al. |
| 8,304,405 B2 | 11/2012 | Lulla et al. |
| 8,318,709 B2 | 11/2012 | Lulla et al. |
| 8,362,078 B2 | 1/2013 | Kiliaan et al. |
| 8,372,451 B2 | 2/2013 | Vuckovic |
| 8,440,243 B2 | 5/2013 | Maewal |
| 8,518,919 B2 | 8/2013 | Dang et al. |
| 8,741,319 B2 | 6/2014 | Crain et al. |
| 8,758,816 B2 | 6/2014 | Fuge et al. |
| 8,859,531 B2 | 10/2014 | Lee et al. |
| 8,865,733 B2 | 10/2014 | Felder |
| 9,119,846 B2 | 9/2015 | Zisapel et al. |
| 9,278,092 B2 | 3/2016 | Chase et al. |
| 9,308,223 B2 | 4/2016 | Maewal |
| 9,504,712 B2 | 11/2016 | Kiliaan et al. |

(Continued)

FOREIGN PATENT DOCUMENTS

| | | |
|---|---|---|
| AU | 2019443520 A1 | 12/2021 |
| AU | 2019445048 A1 | 12/2021 |

(Continued)

OTHER PUBLICATIONS

Ljubenkov et al. Seminars in Neurology, 2016, vol. 36, No. 4, pp. 397-404 (Year: 2016).*
Beitz (Frontiers in Bioscience S6, Jan. 1, 2014, pp. 65-74) (Year: 2014).*
EHealthMe.com "Azelastine and Xanax drug interactions—a phase IV clinical study of FDA data", dated Jan. 7, 2021, 5 pages.
Galatowicz, G, Ajayi Y, Stern ME, Calder VL. Ocular antiallergic compounds selectively inhibit human mast cell cytokines in vitro and conjunctival cell infiltration in vivo. Clin Exp Allergy. 2007; 37:1648-1656.

(Continued)

*Primary Examiner* — James D. Anderson
(74) *Attorney, Agent, or Firm* — New River Valley IP Law, P.C.; Michele L. Mayberry

(57) ABSTRACT

Methods of treating patients suffering from or exhibiting symptoms of mental, behavioral, and/or cognitive disorders with azelastine or a pharmaceutically acceptable salt of azelastine are disclosed.

20 Claims, No Drawings

(56) References Cited

U.S. PATENT DOCUMENTS

| | | | |
|---|---|---|---|
| 9,662,359 | B2 | 5/2017 | Vuckovic |
| 9,700,548 | B2 | 7/2017 | Knutsen et al. |
| 9,844,525 | B2 | 12/2017 | Kiliaan et al. |
| 9,901,585 | B2 | 2/2018 | Lulla et al. |
| 9,919,050 | B2 | 3/2018 | Dang et al. |
| 10,045,915 | B2 | 8/2018 | Glenn, Jr. et al. |
| 10,639,314 | B1 | 5/2020 | Wang et al. |
| 10,639,315 | B1 | 5/2020 | Wang et al. |
| 10,639,316 | B1 | 5/2020 | Wang et al. |
| 10,898,493 | B2 | 1/2021 | Wang et al. |
| 10,946,026 | B2 | 3/2021 | Wang et al. |
| 10,966,989 | B2 | 4/2021 | Wang et al. |
| 11,116,773 | B2 | 9/2021 | Wang et al. |
| 11,318,144 | B2 * | 5/2022 | Wang ............ A61K 31/714 |
| 11,351,179 | B1 | 6/2022 | Wang et al. |
| 11,389,458 | B2 * | 7/2022 | Wang ............ A61K 31/165 |
| 2003/0229030 | A1 | 12/2003 | Theoharides |
| 2005/0163843 | A1 | 7/2005 | Boehm et al. |
| 2006/0051416 | A1 | 3/2006 | Rastogi et al. |
| 2009/0318703 | A1 | 12/2009 | Tani et al. |
| 2010/0152108 | A1 | 6/2010 | Hung et al. |
| 2012/0237570 | A1 | 9/2012 | Crain et al. |
| 2013/0252929 | A1 | 9/2013 | Lee et al. |
| 2014/0127328 | A1 | 5/2014 | Crain et al. |
| 2014/0158117 | A1 | 6/2014 | Dang et al. |
| 2015/0216849 | A1 | 8/2015 | Dedhiya et al. |
| 2016/0166543 | A1 | 6/2016 | Joshi et al. |
| 2017/0035780 | A1 | 2/2017 | Lulla et al. |
| 2018/0104294 | A1 | 4/2018 | Vuckovic |
| 2018/0116979 | A1 | 5/2018 | Clarence-Smith et al. |
| 2020/0323867 | A1 | 10/2020 | Wang et al. |
| 2020/0323868 | A1 | 10/2020 | Wang et al. |
| 2020/0323870 | A1 | 10/2020 | Wang et al. |
| 2020/0323871 | A1 | 10/2020 | Wang et al. |
| 2020/0323873 | A1 | 10/2020 | Wang et al. |
| 2020/0323876 | A1 | 10/2020 | Wang et al. |
| 2020/0323877 | A1 | 10/2020 | Wang et al. |
| 2021/0069209 | A1 | 3/2021 | Wang et al. |
| 2022/0096491 | A1 | 3/2022 | Wang et al. |
| 2022/0168318 | A1 | 6/2022 | Wang et al. |
| 2023/0000882 | A1 | 1/2023 | Wang et al. |

FOREIGN PATENT DOCUMENTS

| | | |
|---|---|---|
| AU | 2019446955 A1 | 12/2021 |
| CA | 3136633 A1 | 10/2020 |
| CA | 3137393 A1 | 11/2020 |
| CA | 3139082 A1 | 11/2020 |
| CN | 113924098 A | 1/2022 |
| CN | 113939276 A | 1/2022 |
| CN | 114072945 A | 2/2022 |
| EP | 3952840 A1 | 2/2022 |
| EP | 3962488 A1 | 3/2022 |
| EP | 3973586 A1 | 3/2022 |
| JP | 2012232978 A | 11/2012 |
| JP | 2016529307 A | 9/2016 |
| JP | 2019019113 A | 2/2019 |
| JP | 2022535644 A | 8/2022 |
| JP | 2022536017 A | 8/2022 |
| JP | 2022539944 A | 9/2022 |
| WO | 02056876 A2 | 7/2002 |
| WO | 2006058022 A1 | 6/2006 |
| WO | 2007061454 A1 | 5/2007 |
| WO | 2014018563 A3 | 5/2014 |
| WO | 2020209872 A1 | 10/2020 |
| WO | 2020222799 A1 | 11/2020 |
| WO | 2020236159 A1 | 11/2020 |
| WO | 2021242235 A1 | 12/2021 |
| WO | 2021242297 A1 | 12/2021 |
| WO | 2021262196 A1 | 12/2021 |
| WO | 2023014361 A1 | 2/2023 |

OTHER PUBLICATIONS

Georgin-Lavialle, S. et al., "Mast Cells' Involvement in Inflammation Pathways Linked to Depression: Evidence in Mastocytosis." Mol Psychiatry. 21 (11), 1511-1516 Nov. 2016.

Goedert, M., Spillantini, M.G,. 2006. A century of Alzheimer's disease. Science, 314:777-81.

Guignet, Michelle et al., "Persistent behavior deficits, neuroinflammation, and oxidative stress in a rat model of acute organophosphate intoxication", vol. 133, Jan. 2020, 101131.

Hansen et al. Clinical Interventions in Aging 2008, vol. 3, No. 2, pp. 211-225.

Hashiro et al. "A Combination Therapy of Psychotropic Drugs and Antihistaminics or Antiallergics in Patients with Chronic Urticaria". Journal of Dermatological Sciences, 1996; 11:209-213.

Hatakeyama, Aiko, Masahiko Fujii, Reiko Hatakeyama, Yumiko Fukuoka, Takuma Satoh-Nakagawa and Hidetada Sasaki, Azelastine hydrochloride on behavioral and psychological symptoms and activities of daily living in dementia patients, Geriatr Gerontol Int 2008; 8: 59-61 (2008).

Hazama, H., Nakajima, T., Hisada, T., Hamada, E., Omata, M., Kurachi, Y. Effects of azelastine on membrane currents in tracheal smooth muscle cells isolated from the guinea-pig. Eur J Pharmacol. 1994;259: 143-150.

Horak, Friedrich, "Effectiveness of twice daily azelastine nasal spray in patients with seasonal allergic rhinitis," Ther. Clin. Risk Manag., Oct. 2008; 4(5): 1009-1022.

Hou, Ruihua and Baldwin, David S., "A neuroimmunological perspective on anxiety disorders", Human Psychopharmacol Clin Exp. 2012, vol. 27: 6-14.

Hou, Ruihua et al., "Peripheral inflammatory cytokines and immune balance in Generalized Anxiety Disorder: case-controlled study", Brain Behav Immun. May 2017; 62: 212-218.

Jeon, Sang Won and Kim, Yong Ku, "Detrimental effect of preservative in eye drops: Neuroinflammation and cytokine abnormality in major depression: Cause or consequence in that illness?" World Journal of Psychiatry, Sep. 22, 2016; 6(3): 283-293.

Kappelmann, N. et al., "Antidepressant activity of anti-cytokine treatment: a systematic review and meta-analysis of clinical trials of chronic inflammatory conditions", Molecular Psychiatry, 2018, vol. 23, 335-313.

Kempuraj, Duraisamy, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231-9 Nov. 2003.

Kohler, Ole et al., "Inflammation in Depression and the Potential for Anti-Inflammatory Treatment." Current Neuropharmacology, 2016, 11, 732-712.

Koo, Ja Wook et al., 2010, Nuclear factor-κB is a critical mediator of stress impaired neurogenesis and depressive behavior. PNAS, Feb. 9, 2010, vol. 107 (6) 2669-2674.

Leon, Michael, Sawmiller, Darrell, Shytle, R. Douglas, and Tan, Jun. 2018. Therapeutic Cocktail Approach for Treatment of Hyperhomocysteinemia in Alzheimer's Disease. Cell Med. 2018; 10: 2155179017722280.

Liu, Chun-Hong et al., Role of inflammation in depression relapse, Journal of Neuroinflammation (2019) 16:90, 11 pages.

Maeng, Sung Ho and Hong, Heeok, "Inflammation as the Potential Basis in Depression." Int Neurourol J 2019; vol. 23(Suppl 2): S63-71.

Naddafi, F., Mirshafiey A., The neglected role of histamine in Alzheimer's disease., Jun. 2013;28(4):327-36. doi: 10.1177/1533317513488925. Epub May 15, 2013.

Niazi, Sarfaraz K., Handbook of Pharmaceutical Manufacturing Formulations vols. 1-6, 2004, 304 pages.

Niraula, Anzela et al., "IL-6 Induced by Social Stress Promotes a Unique Transcriptional Signature in the Monocytes That Facilitate Anxiety." Biol Psychiatry 85 (8), 679-689, Apr. 15, 2019.

Riethmuller et al. Arzneimittel-Forschung, 1994, vol. 44, No. 10, pp. 1136-1140.

Sedeyn, Jonathan Histamine Induces Alzheimer's Disease-Like Blood Brain Barrier Breach and local cellular Responses in Mouse Brain Organotypic Culture. Hindawi. Aug. 21, 2015.

(56) References Cited

OTHER PUBLICATIONS

Simons, F.E., Simons, K.J. Clinical pharmacology of new histamine H1 receptor antagonist. Clin Pharmacokinet. 1999;36:329-352.
Starkstein, et al.,"The construct of generalized anxiety disorder in altheimer's disease," Am J Geriatr Psychiatry Jan. 2007. 15(1) 42-49.
St-Jean, Genevieve; Turcotte, Isabelle; Bastien, Celyne H. Cerebral asymmetry in insomnia sufferers. Frontiers in Neurology 2012, 3, 1-12.
Szelenyi, I. Achterrath-Tuckermann, U. Schmidt, J., Minker, E., Paegelow, I., Werner, H. Azelastine: A multifaceted drug for asthma therapy. Agents Actions Suppl. 1991;34:295-311 (abstract).
Tanaka, Hibiki, Hashimoto, Mamoru, et al., 2015. Relationship Between Dementia Severity and Behavioural and Psychological Symptoms in Early-Onset Alzheimer's Disease. Psychogeriatrics. Dec. 2015;15(4):242-7.
Troubat, Romain et al., Neuroinflammation and Depression: A Review. Eur J Neurosci. Mar. 9, 2020 DOI: 10.1111/ejn.14720.
Williams, Patricia B, Crandall, Elizabeth, and Sheppard, John D, 2010, Azelastine hydrochloride, a dual-acting anti-inflammatory ophthalmic solution, for treatment of allergic conjunctivitis. Clinical Ophthalmology 2010:4 993-1001.
Yoneda, Kazunori, et al. 1997, Suppression by Azelastine Hydrochloride of NF-KB Activation Involved in Generation of Cytokines and Nitric Oxide. Japanese Journal of Pharmacology, 73:145-53.
(Wang, Jianmin) Co-Pending U.S. Appl. No. 16/382,885, filed Apr. 12, 2019, Specification and claims.
(Wang, Jianmin) Co-Pending U.S. Appl. No. 16/398,845, filed Apr. 30, 2019, Specification and Claims.
(Wang, Jianmin) Co-Pending U.S. Appl. No. 16/418,614, filed May 21, 2019, Specification and Claims.
(Wang, Jianmin) Co-pending U.S. Appl. No. 16/424,788, filed May 29, 2019, Specification and Claims.
(Wang, Jianmin) Co-Pending U.S. Appl. No. 16/426,121, filed May 30, 2019, Specification and Claims.
(Wang, Jianmin) Co-Pending U.S. Appl. No. 16/831,330, filed Mar. 26, 2020, Specification and Claims.
(Wang, Jianmin) Co-Pending U.S. Appl. No. 16/834,146, filed Mar. 30, 2020, Specification and Claims.
(Wang, Jianmin) Co-Pending U.S. Appl. No. 16/884,459, filed May 27, 2020, Specification and Claims.
(Wang, Jianmin) Co-Pending U.S. Appl. No. 16/884,553, filed May 27, 2020, Specification and Claims.
(Wang, Jianmin) Co-Pending U.S. Appl. No. 16/913,927, filed Jun. 26, 2020, Specification and Claims.
(Wang, Jianmin) Co-Pending U.S. Appl. No. 17/094,405, filed Nov. 10, 2020, Specification and Claims.
(Wang, Jianmin) Co-Pending U.S. Appl. No. 17/394,898, filed Aug. 5, 2021, Specification and Claims.
(Wang, Jianmin) Co-Pending Application No. PCT/US19/27293, filed Apr. 12, 2019, Specification and Claims.
(Wang, Jianmin) Co-Pending Application No. PCT/US19/29885, Filed Apr. 30, 2019, Specification and Claims.
(Wang, Jianmin) Co-Pending Application No. PCT/US19/33359, Filed May 21, 2019, Specification and Claims.
(Wang, Jianmin) Co-Pending Application No. PCT/US20/34735, filed May 27, 2020, Specification and Claims.
(Wang, Jianmin) Co-Pending Application No. PCT/US20/39916, Filed Jun. 26, 2020, Specification and Claims.
(Wang, Jianmin) Co-Pending Application No. PCT/US20/59846, filed Nov. 10, 2020, Specification and claims.
(Wang, Jianmin) Co-Pending Application No. PCT/US21/44654, filed Aug. 5, 2021, Specification and Claims.
(Wang, Jianmin) Co-Pending Canada National Stage Application based on International Application No. PCT/US19/27293, filed Oct. 8, 2021, Specification and Claims (see PCT/US19/27293).
(Wang, Jianmin) Co-Pending Canada National Stage Application based on International Application No. PCT/US19/29885, Filed Oct. 19, 2021, Specification and Claims (See PCT/US19/29885).
(Wang, Jianmin) Co-Pending China National Stage Application based on International Application No. PCT/US19/27293, filed Oct. 11, 2021, Specification and Claims (see PCT/US19/27293).
(Wang, Jianmin) Co-Pending China National Stage Application based on International Application No. PCT/US19/29885, Filed Oct. 25, 2021, Specification and Claims (See PCT/US19/29885).
(Wang, Jianmin) Co-Pending Japan National Stage Application based on International Application No. PCT/US19/27293, filed Sep. 17, 2021, Specification and Claims (see PCT/US19/27293).
(Wang, Jianmin) Co-Pending Japan National Stage Application based on International Application No. PCT/US19/29885, Filed Sep. 21, 2021, Specification and Claims (See PCT/US19/29885).
Ancill et al. "Agitation in the Demented Elderly: A Role for Benzodiazepines?" International Clinical Psychopharmacology, 1991; 6:141-146.
Bezprozvanny, Ilya. The rise and fall of Dimebon. National Institute of Health. Feb. 12, 2014.
Casale, T. B. The interaction of azelastine with human lung histamine H1, beta, and muscarinic receptor-binding sites. J Allergy Clin Immunol. 1989;83:771-776.
Category H1 receptor antagonists. Wikipedia. Sep. 20, 2012.
Datena-Dell'osso, M. et al., 2011, Inflammatory and Neurodegenerative Pathways in Depression: A New Avenue for Antidepressant Development? Curr Med Chem. 18 (2), 245-55, Abstract, 2 pages.
Ciprandi, G., Pronzato, C., Passalacqua, G., et al. Topical azelastine reduces eosinophil activation and intercellular adhesion molecule-1 expression on nasal epithelial cells: An antiallergic activity. J Allergy Clin Immunol. 1996;98(6 Pt 1):1088-1096.
Conti, Pio et al., "Impact of Mast Cells in Depression Disorder: Inhibitory Effect of IL-37 (New Frontiers)". Immunol Res, vol. 66 (3), 323-331 Jun. 2018.
Co-Pending U.S. Appl. No. 16/382,885, Final office action dated Jun. 5, 2020, 13 pgs.
Co-Pending U.S. Appl. No. 16/382,885, Non-Final office action and list of references dated Nov. 29, 2019, 23 pgs.
Co-Pending U.S. Appl. No. 16/382,885, Non-Final office action dated Dec. 22, 2020, 19 pgs.
Co-Pending U.S. Appl. No. 16/382,885, Notice of Allowance dated Feb. 10, 2021, 9 pages.
Co-Pending U.S. Appl. No. 16/382,885, Response dated Dec. 22, 2020 Non-Final office action filed Jan. 21, 2021, 7 pgs.
Co-Pending U.S. Appl. No. 16/382,885, Response dated Jun. 5, 2020 Final office action filed Jul. 31, 2020, 9 pages.
Co-Pending U.S. Appl. No. 16/382,885, Response dated Nov. 29, 2019 Non-Final office action filed Mar. 2, 2020.
Co-Pending U.S. Appl. No. 16/382,885, Response to restriction requirement dated Oct. 2, 2019, 3pgs.
Co-Pending U.S. Appl. No. 16/382,885, Restriction Requirement dated Aug. 9, 2019, 7 pgs.
Co-Pending U.S. Appl. No. 16/398,845, Interview Summary dated Dec. 18, 2019, 7 pages.
Co-Pending U.S. Appl. No. 16/398,845, Non-Final Office Action dated Aug. 6, 2019, 25 pages.
Co-Pending U.S. Appl. No. 16/398,845, Notice of Allowance dated Jan. 21, 2020, 11 pages.
Co-Pending U.S. Appl. No. 16/398,845, Response to Non-Final Office Action dated Nov. 6, 2019, 9 pages.
Co-Pending U.S. Appl. No. 16/418,614, Interview Summary dated Dec. 18, 2019, 7 pages.
Co-Pending U.S. Appl. No. 16/418,614, Non-Final Office Action dated Aug. 6, 2019, 31 pages.
Co-Pending U.S. Appl. No. 16/418,614, Notice of Allowance dated Jan. 30, 2020, 12 pages.
Co-Pending U.S. Appl. No. 16/418,614. Response to Non-Final Office Action dated Nov. 6, 2019, 10 pages.
Co-Pending U.S. Appl. No. 16/424,788, Corrected Notice of Allowance, dated Jan. 7, 2021, 5 pages.
Co-Pending U.S. Appl. No. 16/424,788 Non-Final Office Action, dated Nov. 29, 2019, 24 pgs.
Co-Pending U.S. Appl. No. 16/424,788 Non-Final Office Action, dated Nov. 5, 2020, 8 pgs.
Co-Pending U.S. Appl. No. 16/424,788 Notice of Allowance, dated Dec. 17, 2020, 9 pages.

(56) References Cited

OTHER PUBLICATIONS

Co-Pending U.S. Appl. No. 16/424,788 Response to Nov. 29, 2019 Non-Final Office Action, filed Mar. 2, 2020.
Co-Pending U.S. Appl. No. 16/424,788 Response to Nov. 5, 2020 Non-Final Office Action, dated Dec. 2, 2020, 6 pages.
Co-Pending U.S. Appl. No. 16/424,788 Response to Restriction Requirement, dated Oct. 2, 2019, 3 pgs.
Co-Pending U.S. Appl. No. 16/424,788 Restriction Requirement, dated Aug. 9, 2019, 7 pgs.
Co-Pending U.S. Appl. No. 16/424,788, Final Office Action dated Aug. 28, 2020, 17 pages.
Co-Pending U.S. Appl. No. 16/424,788, Response to Aug. 28, 2020 Final Office Action filed Oct. 19, 2020, 6 pages.
Co-Pending U.S. Appl. No. 16/426,121, Interview Summary dated Dec. 18, 2019, 7 pages.
Co-Pending U.S. Appl. No. 16/426,121, Non-Final Office Action dated Aug. 6, 2019, 25 pages.
Co-Pending U.S. Appl. No. 16/426,121, Notice of allowance dated Jan. 21, 2020, 18 pages.
Co-Pending U.S. Appl. No. 16/426,121, Response to Non-Final Office Action dated Nov. 6, 2019, 9 pages.
Co-Pending U.S. Appl. No. 16/831,330, Non-Final Office Action dated Apr. 7, 2021, 16 pages.
Co-Pending U.S. Appl. No. 16/831,330, Notice of Allowance dated Aug. 3, 2021, 8 pages.
Co-Pending U.S. Appl. No. 16/831,330, Response to Apr. 7, 2021 Non-Final Office Action filed Jul. 21, 2021, 7 pages.
Co-Pending U.S. Appl. No. 16/884,459, filed Dec. 15, 2020 Final Office Action, 15 pages.
Co-Pending U.S. Appl. No. 16/884,459, Non-Final Office Action dated Aug. 11, 2020, 35 pages.
Co-Pending U.S. Appl. No. 16/884,459, Non-Final Office Action dated Sep. 14, 2021, 35 pages.
Co-Pending U.S. Appl. No. 16/884,459, Response to Aug. 11, 2020 Non-Final Office Action fated Nov. 12, 2020, 11 pages.
Co-Pending U.S. Appl. No. 16/884,459, Response to Dec. 15, 2020 Final Office Action, filed Mar. 15, 2021, 30 pages.
Co-Pending U.S. Appl. No. 16/884,553, Non-Final Office Action dated Aug. 11, 2020, 26 pages.
Co-Pending U.S. Appl. No. 16/884,553, Notice of Allowance dated Dec. 2, 2020, 9 pages.
Co-Pending U.S. Appl. No. 16/884,553, Response to Aug. 11, 2020 Non-Final Office Action dated Nov. 12, 2020, 8 pages.
Co-Pending U.S. Appl. No. 16/913,927, Final Office Action dated Jun. 2, 2021, 16 pages.
Co-Pending U.S. Appl. No. 16/913,927, Non-Final Office Action dated Aug. 11, 2021, 17 pages.
Co-Pending U.S. Appl. No. 16/913,927, Non-Final Office Action dated Feb. 19, 2021, 19 pages.
Co-Pending U.S. Appl. No. 16/913,927, Non-Final Office Action dated Nov. 9, 2020, 24 pages.
Co-Pending U.S. Appl. No. 16/913,927, Response to Aug. 27, 2020 Restriction Requirement, filed Oct. 20, 2020, 5 pages.
Co-Pending U.S. Appl. No. 16/913,927, Response to Feb. 19, 2021 Non-Final Office Action filed May 19, 2021, 10 pages.
Co-Pending U.S. Appl. No. 16/913,927, Response to Jun. 2, 2021 Final Office Action, dated Jul. 30, 2021, 6 pages.
Co-Pending U.S. Appl. No. 16/913,927, Response to Nov. 9, 2020 Non-Final Office Action filed Feb. 5, 2021, 8 pages.
Co-Pending U.S. Appl. No. 16/913,927, Restriction Requirement dated Aug. 27, 2020, 5 pages.
Co-Pending U.S. Appl. No. 17/094,405, Final Office Action dated Jul. 30, 2021, 22 pages.
Co-Pending U.S. Appl. No. 17/094,405, Non-Final Office Action dated Apr. 14, 2021, 21 pages.
Co-Pending U.S. Appl. No. 17/094,405, Response to Apr. 14, 2021 Non-Final Office Action filed Jul. 14, 2021, 7 pages.
Co-Pending U.S. Appl. No. 17/094,405, Response to Jan. 26, 2021 Restriction Requirement, filed Apr. 5, 2021, 7 pages.
Co-Pending U.S. Appl. No. 17/094,405, Response to Jul. 30, 2021 Final Office Action, dated Sep. 30, 2021, 10 pages.
Co-Pending U.S. Appl. No. 17/094,405, Response to Jul. 30, 2021 Final Office Action, filed Sep. 30, 2021, 10 pages.
Co-Pending U.S. Appl. No. 17/094,405, Restriction Requirement dated Jan. 26, 2021, 5 pages.
Co-Pending U.S. Appl. No. 17/394,898, Restriction Requirement dated Oct. 21, 2021, 9 pages.
Co-Pending application No. PCT/US19/29885 International Search Report and Written Opinior dated Jul. 15, 2019. 7 pages.
Co-Pending application No. PCT/US19/33359 International Search Report and Written Opinior dated Aug. 15, 2019. 9 pages.
Co-Pending Application No. PCT/US20/34735, International Search Report and Written Dpinion dated Aug. 17, 2020, 10 pages.
Co-Pending Application No. PCT/US20/39916, International Search Report and Written Opinion dated Oct. 8, 2020, 8 pages.
Co-Pending Application No. PCT/US20/59846, International Search Report and Written Opinion dated Mar. 8, 2021, 8 pages.
Co-Pending Application No. PCT/US2019/027293, Corrected Written Opinion, dated Oct. 29, 2019, 5 pages.
Co-Pending Application No. PCT/US2019/027293, Search Report & Written Opinion, dated Sep. 17, 2019, 8 pages.
Cummings et al. "Effect of Dextromethorphan-Quinidine on Agitation in Patients with Alzheimer Disease Dimentia: A Randomized Clinical Trial". JAMA, 2015; 314(12):1242-1254.
Co-Pending U.S. Appl. No. 17/394,898, Response to Oct. 21, 2021 Restriction Requirement, dated Nov. 10, 2021, 2 pages.
Co-Pending U.S. Appl. No. 17/673,136, Final Office Action dated Feb. 7, 2023, 13 pages.
Co-Pending U.S. Appl. No. 17/673,136, Non-Final Office Action dated Jul. 22, 2022, 20 pages.
Co-Pending U.S. Appl. No. 17/673,136, Response to Feb. 7, 2023 Final Office Action, dated Feb. 21, 2023, 7 pages.
Co-Pending U.S. Appl. No. 17/673,136, Response to Jul. 22, 2022 Non-Final Office Action, dated Dec. 22, 2022, 8 pages.
Co-Pending U.S. Appl. No. 17/673,136, Response to May 3, 2022 Restriction Requirement, dated Jun. 9, 2022, 2 pages.
Co-Pending U.S. Appl. No. 17/673,136, Restriction Requirement dated May 3, 2022, 5 pages.
Co-Pending U.S. Appl. No. 17/940,533, Non-Final Office Action dated Mar. 9, 2023, 21 pages.
Co-Pending U.S. Appl. No. 17/940,533, Preliminary Amendment dated Sep. 8, 2022, 10 pages.
Co-Pending U.S. Appl. No. 17/940,533, Response to Jan. 9, 2023 Restriction Requirement, dated Jan. 24, 2023, 2 pages.
Co-Pending U.S. Appl. No. 17/940,533, Restriction Requirement dated Jan. 9, 2023, 5 pages.
Co-Pending Application No. PCT/US21/44654, International Search Report and Written Dpinion, dated Nov. 15, 2021, 10 pages.
Co-Pending Application No. PCT/US22/16545, International Search Report and Written Opinion dated Jul. 7, 2022, 11 pages.
Co-Pending Application No. PCT/US22/16545, Invitation to Pay Fees dated Apr. 19, 2022, 2 pages.
Co-Pending China National Stage Application No. 201980095322.X, English Version of Amended Claims as filed Oct. 11, 2021, 3 pages.
Co-Pending China National Stage Application No. 201980095322.X, First Office Action (7 pages) dated Jan. 19, 2023 and English Translation (7 pages).
Co-Pending European National Stage Application No. 19924315.5, Extended European Search Report dated Oct. 24, 2022, 6 pages.
Co-Pending European National Stage Application No. 19927207.1, Extended European Search Report dated Nov. 10, 2022, 10 pages.
Co-Pending European National Stage Application No. 19929933.0, Extended European Search Report dated Dec. 14, 2022, 11 pages.
Co-Pending Japan National Stage Application No. 2021-556914 Voluntary Amendment and Request for Exam dated Apr. 11, 2022, JP version (5 pages) and English translation of the amended claims (4 pages).
Co-Pending Japan National Stage Application No. 2021-558496 Voluntary Amendment and Request for Exam dated Apr. 14, 2022, JP version (4 pgs) and English (2 pgs).

(56) References Cited

OTHER PUBLICATIONS

Co-Pending Japan National Stage Application No. 2021-558496, Office Action dated Feb. 24, 2023 (3 pages) and English Translation (4 pages).
Co-Pending Japan National Stage Application No. 2021-566489 Voluntary Amendment and Request for Exam dated May 17, 2022, JP version (5 pgs) and English (4 pgs).
Co-Pending Japan National Stage Application No. 2022-578962, Voluntary Amendment dated Feb. 24, 2023 (3 pages) with English Translation of the Amended Claims (3 pages).
Frisch, C. et al. "The histamine H1-antagonist chlorpheniramine facilitates learning in aged rats", Neuroscience Letters, vol. 229, No. 2, Jun. 27, 1997, pp. 89-92.
Girard, J. et al. "Azelastine protects against CA1 traumatic neuronal injury in the hippocampal slice", European Journal of Pharmacology, vol. 300, Jan. 1, 1996, pp. 43-49.
Hua, S. "Advances in Nanoparticulate Drug Delivery Approaches for Sublingual and Buccal Administration". Nov. 10, 2019 (Article 1328), pp. 1-9.
Lv, Wei-jie et al., "Melatonin Alleviates Neuroinflammation and Metabolic Disorder in DSS-Induced Depression Rats". Oxidative Medicine and Cellular Longevity 2020, Article ID 1241894, 17 pages.
Munoz-Cano et al. "Severity of Allergic Rhinitis Impacts Sleep and Anxiety: Results from a Large Spanish Cohort". Clinical and Translational Allergy, 2018, 8 (Article 23), p. 1-9.
Patki, G. and Y.S. Lau, "Melatonin protects against neurobehavioral and mitochondrial deficits in a chronic mouse model of Parkinson's disease". Pharmacol. Biochem. Behav. 2011, 99: 704-711, 20 pages.
Singh, Tanvir et al. "Alprazolam as a monotherapy for anxiety and depression", Psychiatry (Edgmont). Nov. 2005;(11):32, 1 page.
Tariot, P. N. et al. Memantine Treatment in Patients With Moderate to Severe Alzheimer Disease Already Receiving Donepezil, JAMA, Jan. 21, 2004, vol. 291, No. 3, p. 317-324, 8 pages.
Bennett, F. C. and Molofsky, A. V., "The immune system and psychiatric disease: a basic science perspective", Clinical and Experimental Immunology, May 2019, 197: 291-307.
"Donepezil—Medline Plus", Medline Plus, Dec. 15, 2017, 6 pages, [retrieved Dec. 19, 2022], https://medlineplus.gov/druginfo/meds/a697032.html.
"EPAR summary for the public", European Medicines Agency, Dec. 1, 2012, 3 pages, [retrieved Dec. 19, 2022], https://www.ema.europa.eu/en/documents/overview/prometax-epar-summary-public_en.pdf.
"Razadyne-galantamine hydrobromide tablet, film coated Rebel Distributors Corp", Dailymed, Nov. 11, 2010, 32 pages, [retrieved Dec. 19, 2022], https://dailymed.nlm.nih.gov/dailymed/drugInfo.cfm?setid=e62efb5a-d2cc-4e11-9e61-10e65ef3d897.
(Wang, Jianmin) Co-Pending U.S. Appl. No. 17/546,342, filed Dec. 9, 2021, Specification and Claims.
(Wang, Jianmin) Co-Pending U.S. Appl. No. 17/673,136, filed Feb. 16, 2022, Specification and Claims.
(Wang, Jianmin) Co-Pending U.S. Appl. No. 17/940,533, filed Sep. 8, 2022, Specification and Claims.
(Wang, Jianmin) Co-Pending Application No. PCT/US22/16545, filed Feb. 16, 2022, Specification and Claims.
(Wang, Jianmin) Co-Pending Australia National Stage Application No. 2019443520, Effective-Filing Date Apr. 30, 2019, Specification and Claims (See PCT/US19/29885, which published as WO 2020/222799, for Specification and Claims as filed).
(Wang, Jianmin) Co-Pending Australia National Stage Application No. 2019445048, Effective-Filing Date Apr. 12, 2019, Specification and Claims (See PCT/US19/27293, which published as WO 2020/209872, for Specification and Claims as filed).
(Wang, Jianmin) Co-Pending Australia National Stage Application No. 2019446955, Effective-Filing Date May 21, 2019, Specification and Claims (See PCT/US19/33359, which published as WO2020/236159, for Specification and Claims as filed).
(Wang, Jianmin) Co-Pending Canada National Stage Application No. 3,136,633, filed Oct. 8, 2021, Specification and Claims, 25 pages.
(Wang, Jianmin) Co-Pending Canada National Stage Application No. 3,137,393, Filed Oct. 19, 2021, Specification and Claims, 17 pages.
(Wang, Jianmin) Co-Pending Canada National Stage Application No. 3,139,082, Filed Nov. 3, 2021, Claims and Amended Specification, 25 pages.
(Wang, Jianmin) Co-Pending Canada National Stage Application No. 3,183,560, Filed Dec. 20, 2022, Claims and Specification (See WO2021/262196).
(Wang, Jianmin) Co-Pending China National Stage Application No. 201980095322.X, filed Oct. 11, 2021, Specification and Claims (32 pages) (see PCT/US19/27293, which published as WO2020/209872 for English Translation).
(Wang, Jianmin) Co-Pending China National Stage Application No. 201980095741.3, Filed Oct. 25, 2021, Specification and Amended Claims as filed (26 pages) with English Translation of the Amended Claims (2 pages) (See PCT/US19/29885, which published as WO 2020/222799, for English Translation of the Specification).
(Wang, Jianmin) Co-Pending China National Stage Application No. 201980096574.4, Filed Nov. 18, 2021, Specification and Amended Claims as filed (48 pages) with English Translation of the Amended Claims (4 pages) (See PCT/US19/33359, which published as WO2020/236159, for English Translation of the Specification).
(Wang, Jianmin) Co-Pending China National Stage Application No. 202080102343.2, Filed Dec. 22, 2022, Specification and Amended Claims as filed (28 pages) with English Translation of the Amended Claims (3 pages) (See WO2021/262196, for English Translation of the Specification).
(Wang, Jianmin) Co-Pending European National Stage Application No. 19924315.5, filed Nov. 11, 2021, Specification and Amended Claims as filed (34 pages).
(Wang, Jianmin) Co-Pending European National Stage Application No. 19927207.1, filed Nov. 29, 2021, Specification and Amended Claims as filed (26 pages).
(Wang, Jianmin) Co-Pending European National Stage Application No. 19929933.0, filed Dec. 21, 2021, Specification and Amended Claims as filed (35 pages).
(Wang, Jianmin) Co-Pending European National Stage Application No. 20942038.9, filed Jan. 25, 2023, Specification and Amended Claims as filed (23 pages).
(Wang, Jianmin) Co-Pending Japan National Stage Application No. 2021-556914, filed Sep. 17, 2021, Specification and Claims (19 pages) (see PCT/US19/27293, which published as WO 2020/209872, for English Translation).
(Wang, Jianmin) Co-Pending Japan National Stage Application No. 2021-558496, filed Sep. 21, 2021, Specification and Claims (15 pages) (See PCT/US19/29885, which published as WO 2020/222799, for English Translation).
(Wang, Jianmin) Co-Pending Japan National Stage Application No. 2021-566489, filed Nov. 9, 2021, Request for Entry and Specification and Claims (18 pages) (See PCT/US19/33359, which published as WO2020/236159, for English Translation of Specification and Claims).
(Wang, Jianmin) Co-Pending Japan National Stage Application No. 2022-578962, filed Dec. 21, 2022, Specification and Claims (See WO2021/262196).
Bartlett, D. and Bear, M., "Rhinorrhea as a Result of Alzheimer's Disease Treatment: A Case Report", The Senior Dare Pharmacist. Dec. 2019; 34(10):669-673, 5 pages.
Co-Pending U.S. Appl. No. 16/834,146, Final Office Action dated Mar. 18, 2022, 20 pages.
Co-Pending U.S. Appl. No. 16/834,146, Non-Final Office Action dated Nov. 15, 2021, 29 pages.
Co-Pending U.S. Appl. No. 16/834,146, Notice of Allowance dated Jun. 6, 2022, 8 pages.
Co-Pending U.S. Appl. No. 16/834,146, Response to Mar. 18, 2022 Final Office Action, dated May 12, 2022, 7 pages.
Co-Pending U.S. Appl. No. 16/834,146, Response to Nov. 15, 2021 Non-Final Office Action, dated Feb. 22, 2022, 9 pages.

(56) References Cited

OTHER PUBLICATIONS

Co-Pending U.S. Appl. No. 16/884,459, Applicant-Initiated Interview Summary dated Apr. 5, 2022, 2 pages.
Co-Pending U.S. Appl. No. 16/884,459, Applicant-Initiated Interview Summary dated Jun. 24, 2022, 2 pages.
Co-Pending U.S. Appl. No. 16/884,459, Final Office Action dated Dec. 10, 2021, 19 pages.
Co-Pending U.S. Appl. No. 16/884,459, Non-Final Office Action dated Aug. 30, 2022, 32 pages.
Co-Pending U.S. Appl. No. 16/884,459, Response to Aug. 30, 2022 Non-Final Office Action, filed Nov. 21, 2022, 12 pages.
Co-Pending U.S. Appl. No. 16/884,459, Response to Dec. 10, 2021 Final Office Action, filed Feb. 25, 2022, 18 pages.
Co-Pending U.S. Appl. No. 16/884,459, Response to Sep. 14, 2021 Non-Final Office Action, filed Nov. 16, 2021, 9 pages.
Co-Pending U.S. Appl. No. 16/884,459, Rule 132 Declaration dated Feb. 24, 2022, 4 pages.
Co-Pending U.S. Appl. No. 16/884,459, Rule 132 Declaration dated Nov. 18, 2022, 52 pages.
Co-Pending U.S. Appl. No. 16/913,927, Final Office Action dated Dec. 3, 2021, 12 pages.
Co-Pending U.S. Appl. No. 16/913,927, Notice of Allowance dated Mar. 21, 2022, 11 pages.
Co-Pending U.S. Appl. No. 16/913,927, Response to Aug. 11, 2021 Non-Final Office Action, dated Nov. 10, 2021, 6 pages.
Co-Pending U.S. Appl. No. 16/913,927, Response to Dec. 3, 2021 Final Office Action, dated Mar. 3, 2022, 3 pages.
Co-Pending U.S. Appl. No. 17/094,405, Non-Final Office Action dated Apr. 14, 2022, 38 pages.
Co-Pending U.S. Appl. No. 17/394,898, Examiner-Initiated Interview Summary for Interview conducted Mar. 4, 2022, 1 page.
Co-Pending U.S. Appl. No. 17/394,898, Non-Final Office Action dated Nov. 24, 2021, 9 pages.
Co-Pending U.S. Appl. No. 17/394,898, Notice of Allowance and Examiner's Amendment dated Mar. 17, 2022, 13 pages.
Co-Pending U.S. Appl. No. 17/394,898, Response to Nov. 24, 2021 Non-Final Office Action, dated Feb. 23, 2022, 9 pages.
Co-Pending U.S. Appl. No. 17/673,136, Applicant-Initiated Interview Summary dated Apr. 7, 2023, 2 pages.
Co-Pending U.S. Appl. No. 17/673,136, Non-Final Office Action dated Apr. 4, 2023, 11 pages.
Co-Pending China National Stage Application No. 201980095741.3, Office Action dated Mar. 23, 2023 (8 pages) and English Translation (9 pages).
Co-Pending Japan National Stage Application No. 2021-566489, Office Action dated Mar. 29, 2023 (5 pages) and English Translation (7 pages).
Sors, A. et al., "The Synergistic Enhancing-Memory Effect of Donepezil and S 38093 (a Histamine H3 Antagonist) Is Mediated by Increased Neural Activity in the Septo-hippocampal Circuitry in Middle-Aged Mice", Frontiers in Pharmacology, 2016, vol. 7, No. 492, pp. 1-12.
Co-Pending U.S. Appl. No. 16/884,459, Final Office Action dated Apr. 27, 2023, 20 pages.
Co-Pending U.S. Appl. No. 17/673,136, Applicant-Initiated Interview Summary dated May 1, 2023, 5 pages.
Co-Pending U.S. Appl. No. 17/673,136, Response to Apr. 4, 2023 Non-Final Office Action, dated May 2, 2023, 6 pages.

\* cited by examiner

METHOD OF TREATING DEMENTIA

CROSS-REFERENCE TO RELATED APPLICATIONS

The present application is a Continuation application of U.S. patent application Ser. No. 16/831,330 filed Mar. 26, 2020 (published as U.S. Patent Publication No. 2020/0323870), which application is a Continuation application of U.S. patent application Ser. No. 16/426,121 filed May 30, 2019, which issued as U.S. Pat. No. 10,639,316 on May 5, 2020. The '121 application is a Continuation application of U.S. patent application Ser. No. 16/398,845 filed Apr. 30, 2019, which issued as U.S. Pat. No. 10,639,314 on May 5, 2020. The '330 application is a Continuation-in-Part application of U.S. patent application Ser. No. 16/424,788 filed May 29, 2019, which issued as U.S. Pat. No. 10,946,026 on Mar. 16, 2021, and is a Continuation-in-Part application of U.S. patent application Ser. No. 16/418,614 filed May 21, 2019, which issued as U.S. Pat. No. 10,639,315 on May 5, 2020. The '788 application is a Continuation application of U.S. patent application Ser. No. 16/382,885 filed Apr. 12, 2019, which issued as U.S. Pat. No. 10,966,989 on Apr. 6, 2021. The '330 application is a Continuation-in-Part application of International Application No. PCT/US19/33359 filed May 21, 2019 (which published as International Publication No. WO 2020/236159 on Nov. 26, 2020), and is a Continuation application of International Application No. PCT/US19/29885 filed Apr. 30, 2019 (which published as International Publication No. WO 2020/222799 on Nov. 5, 2020), and is a Continuation-in-Part application of International Application No. PCT/US19/27293 filed Apr. 12, 2019 (which published as International Publication No. WO 2020/209872 on Oct. 15, 2020). All of the foregoing applications are hereby incorporated herein by reference in their entireties.

FIELD OF THE INVENTION

The invention relates to the field of practical medicine, namely, to the use of pharmaceutical compositions exhibiting a neurotropic action, alleviating manifestations of mental, behavioral, or cognitive disorders in cases of organic damage of various origin to the central nervous system.

BACKGROUND OF THE INVENTION

Alzheimer's disease (AD) is a progressive, chronic neurodegenerative disease that usually starts slowly and gradually worsens over time. AD is the most common cause of dementia among older adults. Dementia is the loss of cognitive functioning—thinking, remembering, and reasoning—and behavioral abilities to such an extent that it interferes with a person's daily life and activities. In its early stages, memory loss is mild, but with late-stage AD, individuals lose the ability to carry on a conversation and respond to their environment. If untreated, AD ultimately leads to death. Although the speed of progression can vary, the typical life expectancy following diagnosis is three to nine years.

A central mechanism in learning and memory is long-term potentiation (LTP). LTP is mediated by the neurotransmitter glutamate via the N-Methyl-D-aspartic acid (NMDA) receptor. The NMDA receptors can be found diffusely throughout the brain. However, they densely populate the dendrites of pyramidal cells in the hippocampus and cortex (areas known to be involved in cognition, learning, and memory). In addition to the relationship between LTP and learning, elevated glutamate levels are associated with excitotoxicity. Chronic low-dose administration of NMDA receptor agonists has been shown to induce apoptosis, while high doses induce necrosis. The activation of glutamate receptors has also been found to induce the release of glutamate. Thus, a large build-up of glutamate can occur and induce a massive accumulation of Ca2+, leading to apoptosis. It was also noted that amyloid-beta (AB) plaques increase a neuron's vulnerability to excitotoxicity. AB plaques, a pathological feature of AD, were found to induce depolarization of astrocytes, extracellular accumulation of glutamate, and intracellular deposition of Ca2+. Therefore, the glutamate-induced excitotoxicity pathway made an excellent target for the therapy of AD.

Under physiologic conditions, the glutamate released by neurons is metabolized or taken up by neighboring cells. When these pathways are disrupted, the accumulated glutamate overexcites the NMDA receptor and induces pathology characteristic of neurodegenerative diseases. NMDA receptors act as a calcium [II] ion (Ca2+) channel that activates when bound by glycine, glutamate, and/or NMDA. However, the channel functions only when the cell membrane is depolarized due to the blockade of the channel by the magnesium [II] ion (Mg2+). This prevents the influx of Ca2+ when the neuron is at rest. Under pathological conditions, such as a chronically depolarized membrane, Mg2+ leaves the channel and neuronal metabolism is inhibited, leading to cell death. When this happens, the Ca2+ influx is unrestricted for a longer period of time than normal. This influx of Ca2+ contributes to an alteration of cell function, leading to cell death either through free radicals or through overload of the mitochondria, resulting in free radical formation, caspase activation, and the release of apoptosis-inducing factors. Antagonists to the NMDA vary in affinity and in site of action, resulting in different alterations to the channel. Regardless of the mechanism of action, antagonists decrease the permeability of the channel and prevent an influx of Ca2+. Thus NMDA receptor antagonists are looked to as possible neuroprotective agents and potential therapies for neurodegenerative disease.

Most NMDA antagonists are competitive antagonists and are not well tolerated by patients due to side effects, which can include hallucinations and schizophrenia-type symptoms. The side effects likely result from the competitive antagonists blocking physiological functions of the NMDA receptor. Its role in cognition, memory, and learning make it necessary that any drug using the NMDA receptor as a target of action must preserve physiologic function to be therapeutically useful. Memantine acts on activated NMDA receptors by binding to a site located in the channel of the receptor. However, memantine will not cure AD or prevent the loss of these abilities at some time in the future. So AD has no current cure, and our effort is to find better ways to reverse the disease, delay and prevent it from developing.

On the other hand, the genetic, cellular, and molecular changes associated with AD support the evidence that activated immune and inflammatory processes is a part of the disease. Also a strong benefit of long-term use of NSAIDs was shown in epidemiological studies. So it is generally accepted that AD is partially an inflammatory disease and that inhibiting inflammation is an option of treating AD.

Inflammation clearly occurs in pathologically vulnerable regions of the AD brain, and it does so with the full complexity of local peripheral inflammatory responses. In the periphery, degenerating tissue and the deposition of highly insoluble abnormal materials are classical stimulants of inflammation. Likewise, in the AD brain damaged neurons and neurites and highly insoluble amyloid β peptide deposits and neurofibrillary tangles provide obvious stimuli for inflammation. Because these stimuli are discrete, micro-localized, and present from early preclinical to terminal stages of AD, local upregulation of complement, cytokines, acute phase reactants, and other inflammatory mediators is also discrete, micro-localized, and chronic. Cumulated over many years, direct and bystander damage from AD inflammatory mechanisms is likely to significantly exacerbate the very pathogenic processes that gave rise to it. Thus, animal models and clinical studies so far strongly suggest that AD inflammation significantly contributes to AD pathogenesis. By better understanding AD inflammatory and immune-regulatory processes, it should be possible to develop anti-inflammatory approaches that may reverse or delay or prevent developing of this devastating disorder.

Azelastine is classified pharmacologically as a second generation antihistamine and is a relatively selective, non-sedating, competitive antagonist at H1 receptors. More uniquely, its inhibition of inflammatory mediators, in addition to antihistaminic and mast cell stabilizing effects, places it among the new generation of dual-acting anti-inflammatory drugs. In addition to azelastine's high affinity for H1 receptors, its ability to modify several other mediators of inflammation and allergy contributes to its mechanism of action. In vitro and in vivo studies, as well as clinical trials support the dual effects of direct inhibition and stabilization of inflammatory cells. In vitro data indicate that azelastine's affinity for H1 receptors is estimated to be several times greater than that of chlorpheniramine, a first-generation H1 antagonist. Azelastine has only weak affinity for H2 receptors. Release of histamine from mast cells is also inhibited possibly by reversible inhibition of voltage-dependent L-type calcium channels. Inhibition of mast cell degranulation may also decrease the release of other inflammatory mediators, including leukotrienes and interleukin-1β, among others. Azelastine also directly antagonizes other mediators of inflammation, such as tumor necrosis factor-α, leukotrienes, endothelin-1, and platelet-activating factor.

SUMMARY OF THE INVENTION

The present invention includes the discovery of a method of administering azelastine or a pharmaceutically acceptable salt of azelastine to patients for treating mental, behavioral, cognitive disorders.

In some embodiments of this invention, the pharmaceutically acceptable salt of azelastine is azelastine hydrochloride.

In some embodiments of this invention, azelastine hydrochloride is provided in a daily effective amount of about 4 mg to about 40 mg.

The present invention also includes an oral pharmaceutical dosage form of the pharmaceutically acceptable salt form of azelastine that is a solid form or a liquid form.

The present invention further includes the medical use of the oral pharmaceutical dosage form of azelastine or a pharmaceutically acceptable salt of azelastine which includes administering the dosage form to patients with mental, behavioral, cognitive disorders, such as Alzheimer's disease, vascular dementia, Huntington's disease, frontal temporal dementia, traumatic brain injury, corticobasal degeneration, and/or Parkinson's disease.

In some embodiments of this invention, an oral pharmaceutical dosage form of azelastine hydrochloride in a daily effective amount of about 8 mg to about 16 mg is administered to patients with Alzheimer's disease once daily or twice daily.

DETAILED DESCRIPTION OF THE INVENTION

The inventors of the present invention surprisingly found that higher oral dosages of azelastine or a pharmaceutically acceptable salt of azelastine are suitable for treating patients suffering from mental, behavioral, cognitive disorders.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Definitions

As used in the present specification, the following words and phrases are generally intended to have the meanings as set forth below, except to the extent that the context in which they are used indicates otherwise.

Mental, behavioral, cognitive disorders include Alzheimer's disease, vascular dementia, Huntington's disease, frontal temporal dementia, traumatic brain injury, corticobasal degeneration, or Parkinson's disease, and combinations of any thereof and other neurodegenerative disorders.

As used herein, the term "azelastine" refers to azelastine free base, or 4-(p-Chlorobenzyl)-2-(hexahydro-1-methyl-1H-azepin-4-yl)-1-(2H)-phthalazinone. In certain embodiments, azelastine also includes any pharmaceutically acceptable salt, such as the hydrochloride or HCl salt. Preferably, in any embodiments of the invention as described herein, azelastine is in the form of its hydrochloride salt, as azelastine hydrochloride or azelastine HCl. More preferably, in any embodiment of the invention as described herein, reference to the amounts and dosage ranges of azelastine in the oral dosage forms are to the amounts and dosage ranges of azelastine hydrochloride.

As used herein, the term "pharmaceutically acceptable salt" refers to a salt of azelastine formed with an acid selected from a group of acids consisting of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), undecylenic acid.

As used herein, "treating" or "treatment" means complete cure or incomplete cure, or it means that the symptoms of the underlying disease or associated conditions are at least reduced and/or delayed, and/or that one or more of the underlying cellular, physiological, or biochemical causes or mechanisms causing the symptoms are reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is therapeutically sufficient to effect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutically acceptable salt of azelastine may be administered in either single or multiple doses by oral administration. Administration may be via capsule, tablet, or the like.

As used herein, the term "about" used in the context of quantitative measurements means the indicated amount ±10%. For example, with a ±10% range, "about 5 mg" can mean 4.5-5.5.

The oral dosage forms of azelastine or a pharmaceutically acceptable salt of azelastine in the amount of from about 4 mg to about 40 mg may be formulated for pharmaceutical use using methods known in the art, for example, Ansel's Pharmaceutical Dosage Forms and Drug Delivery Systems Tenth (by Loyd Allen, 2013) and Handbook of Pharmaceutical Manufacturing Formulations (Volumes 1-6 by Sarfaraz K. Niazi). Accordingly, incorporation of the active compounds and a controlled, or slow release matrix may be implemented.

Either fluid or solid unit dosage forms can be readily prepared for oral administration. For example, admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent subjects, sustained release formulations may even be preferred. Capsules may be formulated by mixing the compound with a pharmaceutical diluent which is inert and inserting this mixture into a hard gelatin capsule having the appropriate size. If soft capsules are desired, a slurry of the pharmaceutically acceptable salt of azelastine with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or a biological sweetener and a flavoring agent in the form of an elixir.

The solid oral dosage formulation of the pharmaceutically acceptable salt of azelastine in this disclosure means a form of tablets, caplets, bi-layer tablets, film-coated tablets, pills, capsules, or the like. Tablets in accordance with this disclosure can be prepared by any mixing and tableting techniques that are well known in the pharmaceutical formulation industry. In some examples, the dosage formulation is fabricated by direct compressing the respectively prepared sustained-release portion and the immediate-release portion by punches and dies fitted to a rotary tableting press, ejection or compression molding or granulation followed by compression.

The pharmaceutically acceptable salt of azelastine provided in accordance with the present disclosure are usually administered orally. This disclosure therefore provides a pharmaceutically acceptable salt of azelastine that comprise a solid dispersion comprising a pharmaceutically acceptable salt of azelastine in the amount of from about 4 mg to about 40 mg as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical art (see, e.g., Ansel's Pharmaceutical Dosage Forms and Drug Delivery Systems, Tenth (by Loyd Allen, 2013) and Handbook of Pharmaceutical Manufacturing Formulations (Volumes 1-6 by Sarfaraz K. Niazi)).

The pharmaceutically acceptable salt of azelastine in the amount of from about 4 mg to about 40 mg may further comprise pharmaceutical excipients such as diluents, binders, fillers, glidants, disintegrants, lubricants, solubilizers, and combinations thereof. Some examples of suitable excipients are described herein. When the pharmaceutically acceptable salt of azelastine in the amount of from about 4 mg to about 40 mg is formulated into a tablet, the tablet may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In certain embodiments, the pharmaceutically acceptable salts of azelastine are administered as daily effective amounts of from about 4 mg to about 40 mg of azelastine HCl or from about 4 mg to about 20 mg of azelastine HCl or from about 8 mg to about 16 mg of azelastine HCl.

Preferred are compositions formulated to deliver azelastine or a salt thereof in an amount of up to about 20 mg per day (such as from about 1-20 mg, or 2-19 mg, or 3-18 mg, or 4-17 mg, or 5-15 mg, or 6-12 mg, or 8-10 mg, or 3-11 mg, or 2-13 mg, or 7-16 mg, and so on), and donepezil or a salt thereof in an amount of up to about 23 mg per day (such as from about 1-23 mg, or 2-22 mg, or 3-20 mg, or 4-18 mg, or 5-16 mg, or 6-15 mg, or 7-12 mg, or 1.5-3 mg, or 1-2 mg, or 2.5-5 mg, and so on).

It will be understood, that the amount of azelastine HCl actually administered usually will be determined by a physician, in the light of the relevant circumstances, including the condition to be treated, the chosen route of administration, the age, weight and response of the individual patient, the severity of the patient's symptoms, and the like.

The pharmaceutically acceptable salts of azelastine as described herein are administered to a patient suffering from mental, behavioral, cognitive disorders and other neurodegenerative disorders, such as Alzheimer's disease, with a daily effective amount of from about 4 mg to about 40 mg by oral administration once daily, twice daily, once every other day, once a week, two times a week, three times a week, four times a week, or five times a week.

In some embodiments, the pharmaceutical dosage forms, and tablets of the pharmaceutically acceptable salts of azelastine in a daily effective amount of from about 4 mg to about 40 mg as described in this specification are effective for reversing symptoms in patients suffering from early, middle or late stage Alzheimer's disease in about 6-24 weeks.

The following Examples are illustrative and should not be interpreted to limit the scope of the claimed subject matter. The Examples show that after 6 months of treatment with 12 mg azelastine HCl, both patients improved significantly on memory, language, reasoning, and time arrangement. Mini-Mental State Examination (MMSE) was not assessed but it is reasonable to predict that MMSE would have been significantly improved if measured.

EXAMPLE 1

An 80 year old female patient with a weight of 51 kilograms and diagnosed with late-stage Alzheimer's disease for 6 years required round-the-clock assistance for her daily activities such as walking and looking for things, as well as personal care and her speech was limited to only a few words. She had very little awareness of her surroundings before being treated with 12 mg azelastine HCl once daily before bedtime. After 6 weeks of treatment with 12 mg azelastine HCl once daily before bedtime, she was able to walk in her house with light assistance. After 12 weeks of treatment, she was able to speak for more than 1 minute, know activities in her house and ask questions about daily activities in her house. After 6 months of treatment, she was a completely different person in terms of what she was able to do in comparison to what she could do before treatment, and she could actively talk to people and did not require assistance for her daily activities and personal care. Accordingly, her MMSE scores would similarly have been expected to have improved. Her weight gained by 3 kilograms after the 6 month treatment.

EXAMPLE 2

An 83 year old female with a weight of 49 kilograms was diagnosed with mid- to late-stage Alzheimer's disease. Her daily activities were limited because she couldn't recall things which just occurred and could not locate anything that she wanted to retrieve by herself. She required assistance for most of her daily activities including personal care before she started the treatment of 12 mg azelastine HCl once daily before bedtime. After 6 weeks of treatment, she started to show signs that she was able to find a few things which she intended to retrieve. After 3 months of treatment, she required assistance for only a few daily activities or personal care and could do most of them by herself. Her MMSE scores would similarly have been expected to have improved. Her weight gained by 2.5 kilograms after the 6 month treatment.

REFERENCES

Sucher N J, Lipton S A, Dreyer E B. Molecular basis of glutamate toxicity in retinal ganglion cells. Vision Res. 1997; 37(24):3483-3493.

Koh J Y, Yang L L, Cotman C W. Beta-amyloid protein increases the vulnerability of cultured cortical neurons to excitotoxic damage. Brain Res. 1990; 533(2):315-320.

Harkany T, Abraham I, Timmerman W, et al. Beta-amyloid neurotoxicity is mediated by a glutamate-triggered excitotoxic cascade in rat nucleus basalis. Eur J Neurosci. 2000; 12(8):2735-2745.

Zeevalk G D, Nicklas W J. Evidence that the loss of the voltage-dependent Mg2+ block at the N-methyl-D-aspartate receptor underlies receptor activation during inhibition of neuronal metabolism. J Neurochem. 1992; 59(4):1211-1220.

Lipton S A, Nicotera P. Calcium, free radicals and excitotoxins in neuronal apoptosis. Cell Calcium. 1998; 23:2-3. 165-171.

Gelosa P, Colazzo F, Tremoli E, Sironi L, Castiglioni L. Cysteinyl Leukotrienes as Potential Pharmacological Targets for Cerebral Diseases. Mediators Inflamm. 2017 May 10.

Alzheimer's Disease International, "World Alzheimer Report 2010: the global economic impact of dementia."

R. S. Doody, J. K. Dunn, C. M. Clark et al., "Chronic donepezil treatment is associated with slowed cognitive decline in Alzheimer's disease," Dementia and Geriatric Cognitive Disorders, vol. 12, no. 4, pp. 295-300, 2001.

E. Schwam and Y. Xu, "Cognition and function in Alzheimer's disease: Identifying the transitions from moderate to severe disease," Dementia and Geriatric Cognitive Disorders, vol. 29, no. 4, pp. 309-316, 2010.

M. R. Farlow, M. L. Miller, and V. Pejovic, "Treatment options in Alzheimer's disease: maximizing benefit, managing expectations," Dementia and Geriatric Cognitive Disorders, vol. 25, no. 5, pp. 408-422, 2008.

A. Atri, L. W. Shaughnessy, J. J. Locascio, and J. H. Growdon, "Long-term course and effectiveness of combination therapy in Alzheimer disease," Alzheimer Disease and Associated Disorders, vol. 22, no. 3, pp. 209-221, 2008.

A. Atri, S. D. Rountree, O. L. Lopez, and R. S. Doody, "Validity, significance, strengths, limitations, and evidentiary value of real-world clinical data for combination therapy in Alzheimer's disease: comparison of efficacy and effectiveness studies," Neurodegenerative Diseases, vol. 10, no. 1-4, pp. 170-174, 2012.

C. W. Zhu and M. Sano, "Economic considerations in the management of Alzheimer's disease," Clinical interventions in aging, vol. 1, no. 2, pp. 143-154, 2006.

Epstein A B, van Hoven P T, Kaufman A, Carr W W. Management of allergic conjunctivitis: An evaluation of the perceived comfort and therapeutic efficacy of olopatadine 0.2% and azelastine 0.05% from two prospective studies. Clin Ophthalmol. 2009; 3:329-336.

Bielory L, Bielory B. Ocular allergy: An allergist's perspective. Aug. 16, 2010.

Pflugfelder S C. Prevalence, burden, and pharmacoeconomics of dry eye disease. Am J Manag Care. 2008; 14 Suppl 3:S102-S106.

Bielory L, Lien K W, Bigelsen S. Efficacy and tolerability of newer antihistamines in the treatment of allergic conjunctivitis. Drugs. 2005; 65:215-218.

Bielory L, Buddiga P, Bigelsen S. Ocular allergy treatment comparisons: Azelastine and olopatadine. Curr Allergy Asthma Rep. 2004; 4:320-325.

Baudouin C. Detrimental effect of preservative in eye drops: Implications for the treatment of glaucoma. Acta Ophthalmologica. 2008; 86:716-726.

Lee J S, Lee J E, Kim N, Oum B S. Comparison of the conjunctival toxicity of topical ocular antiallergic agents. J Ocul Pharmacol Ther. 2008; 24:557-562.

Lambiase A, Micera A, Bonini S. Multiple action agents and the eye: Do they really stabilize mast cells? Curr Opin Allergy Clin Immunol. 2009; 9:454-465.

Casale T. The interaction of azelastine with human lung histamine H1, beta, and muscarinic receptor-binding sites. J Allergy Clin Immunol. 1989; 83:771-776.

Hazama H, Nakajima T, Hisada T, Hamada E, Omata M, Kurachi Y. Effects of azelastine on membrane currents in tracheal smooth muscle cells isolated from the guinea-pig. Eur J Pharmacol. 1994; 259: 143-150.

Perhach J L, Connell J T, Kemp J P. Treatment of upper and lower airway disease with azelastine. N Engl Reg Allergy Proc. 1987; 8:121-124.

Szelenyi I, Achterrath-Tuckermann U, Schmidt J, Minker E, Paegelow I, Werner H. Azelastine: A multifaceted drug for asthma therapy. Agents Actions Suppl. 1991; 34:295-311.

Galatowicz G, Ajayi Y, Stern M E, Calder V L. Ocular antiallergic compounds selectively inhibit human mast cell cytokines in vitro and conjunctival cell infiltration in vivo. Clin Exp Allergy. 2007; 37:1648-1656.

Ciprandi G, Pronzato C, Passalacqua G, et al. Topical azelastine reduces eosinophil activation and intercellular adhesion molecule-1 expression on nasal epithelial cells: An antiallergic activity. J Allergy Clin Immunol. 1996; 98(6 Pt 1):1088-1096.

Simons F E, Simons K J. Clinical pharmacology of new histamine H1 receptor antagonist. Clin Pharmacokinet. 1999; 36:329-352.

Loyd Allen, Ansel's Pharmaceutical Dosage Forms and Drug Delivery Systems, Tenth (2013). Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method of treating dementia comprising:
   administering to a patient having dementia about 8-12 mg azelastine or a pharmaceutically acceptable salt of azelastine for a period of time to treat one or more symptoms of dementia.

2. The method of claim 1, wherein the pharmaceutically acceptable salt of azelastine is a salt of azelastine formed with an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), undecylenic acid, or combinations thereof.

3. The method of claim 1, wherein the pharmaceutically acceptable salt of azelastine is azelastine hydrochloride.

4. The method of claim 1, wherein the azelastine or the pharmaceutically acceptable salt of azelastine is administered by way of sustained release.

5. The method of claim 1, wherein the azelastine or the pharmaceutically acceptable salt of azelastine is administered in the amount of about 8-10 mg daily.

6. The method of claim 1, wherein the azelastine or the pharmaceutically acceptable salt of azelastine is administered in the amount of about 8 mg daily.

7. The method of claim 1, wherein the patient has Alzheimer's disease, Parkinson's disease, Huntington's disease, traumatic brain injury, vascular dementia, frontal temporal dementia, or corticobasal degeneration.

8. The method of claim 7, wherein the patient has Huntington's disease.

9. The method of claim 1, wherein the azelastine or the pharmaceutically acceptable salt of azelastine is administered once daily or twice daily.

10. The method of claim 1, wherein one or more of the symptoms of dementia are chosen from reduced: awareness, memory, language, speech, reasoning, mobility, or time arrangement skills of the patient, or combinations thereof.

11. The method of claim 8, wherein the azelastine or the pharmaceutically acceptable salt of azelastine is administered in the amount of about 8-10 mg daily.

12. The method of claim 11, wherein the azelastine or the pharmaceutically acceptable salt of azelastine is administered in the amount of about 8 mg daily.

13. A method comprising administering to a patient having Huntington's disease about 4 mg to about 8 mg azelastine, or a pharmaceutically acceptable salt of azelastine for a period of time to treat one or more symptoms of the patient's Huntington's disease.

14. The method of claim 13, wherein one or more symptoms of the patient's Huntington's disease improve with the administering and are chosen from motor skills, cognition skills, or behavior, or combinations thereof.

15. The method of claim 13, wherein the pharmaceutically acceptable salt of azelastine is a salt of azelastine formed with an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (-L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (-L), salicylic acid, sebacic acid, stearic acid, succinic acid, sulfuric acid, tartaric acid (+L), thiocyanic acid, toluenesulfonic acid (p), undecylenic acid, or combinations thereof.

16. The method of claim 13, wherein the pharmaceutically acceptable salt of azelastine is azelastine hydrochloride.

17. The method of claim 13, wherein the azelastine or the pharmaceutically acceptable salt of azelastine is administered by way of sustained release.

18. The method of claim 13, wherein the azelastine or the pharmaceutically acceptable salt of azelastine is administered once daily or twice daily.

19. The method of claim 7, wherein the patient has Alzheimer's disease.

20. The method of claim 7, wherein the patient has Parkinson's disease.

* * * * *